US012704498B2

(12) United States Patent
Hong

(10) Patent No.: US 12,704,498 B2
(45) Date of Patent: Aug. 11, 2026

(54) INSTALLATION STRUCTURE FOR GREASE SENSOR

(71) Applicant: Aktiebolaget SKF, Gothenburg (SE)

(72) Inventor: Zhichao Hong, Shanghai (CN)

(73) Assignee: Aktiebolaget SKF, Gothenburg (SE)

( * ) Notice: Subject to any disclaimer, the term of this patent is extended or adjusted under 35 U.S.C. 154(b) by 282 days.

(21) Appl. No.: 18/487,292

(22) Filed: Oct. 16, 2023

(65) Prior Publication Data

US 2024/0133861 A1 Apr. 25, 2024
US 2024/0230618 A9 Jul. 11, 2024

(30) Foreign Application Priority Data

Oct. 25, 2022 (CN) ........................ 202211310454.X

(51) Int. Cl.
*G01N 33/30* (2006.01)
*G01N 33/28* (2006.01)

(52) U.S. Cl.
CPC ................................ *G01N 33/2888* (2013.01)

(58) Field of Classification Search
CPC ...... G01N 33/26; G01N 33/28; G01N 33/288; H01R 13/52; H01R 13/5202; H01R 13/5205; H01R 13/5219; H01R 13/5221; G01D 11/24; G01D 11/245; G01D 11/30; G01D 11/305
See application file for complete search history.

(56) References Cited

U.S. PATENT DOCUMENTS 3,788,655 A * 1/1974 Hathaway ................. F16L 5/10 16/2.2
6,127,819 A * 10/2000 Ouchi ..................... G01P 3/487 324/173
6,161,417 A * 12/2000 Nepsund ............. B01D 46/446 116/270
6,196,057 B1 * 3/2001 Discenzo ............. F16C 33/667 73/54.01
6,254,276 B1 * 7/2001 Ouchi ................... F16C 33/723 324/207.25
7,020,931 B1 * 4/2006 Burnett ............... B60R 16/0222 174/152 G
7,918,486 B2 * 4/2011 Preisendorfer ....... F16L 41/088 285/215
8,471,161 B2 * 6/2013 Chou ....................... H01H 1/58 200/61.45 R
2004/0200278 A1 * 10/2004 Gansebom ............ H01H 36/02 73/322.5

(Continued)

FOREIGN PATENT DOCUMENTS

EP 2657554 A1 * 10/2013 .............. F16C 23/08

*Primary Examiner* — Herbert K Roberts
(74) *Attorney, Agent, or Firm* — Stinson LLP

(57) ABSTRACT

An installation structure for grease sensor includes a housing having a through-hole. A resilient grommet is installed in the through-hole. The resilient grommet has an installation hole. A probe of the grease sensor extends from a base and is inserted into said installation hole such that the end of the probe extends into the interior of the housing to contact the grease. The inner surface of the resilient grommet is resiliently pressed against the outer surface of the probe to form a tightly sealing interface. This kind of installation structure allows effective grease sealing, and convenient and stable installation.

14 Claims, 4 Drawing Sheets

(56) References Cited

U.S. PATENT DOCUMENTS

| | | | | |
|---|---|---|---|---|
| 2005/0183522 | A1* | 8/2005 | Smith | G01D 11/245 73/866.5 |
| 2007/0216105 | A1* | 9/2007 | Fessele | G01L 19/0007 277/318 |
| 2015/0008032 | A1* | 1/2015 | Nakai | H02G 15/013 174/650 |
| 2019/0242470 | A1* | 8/2019 | Schmidt | F16J 15/3204 |
| 2020/0041069 | A1* | 2/2020 | Fitch | F16N 29/00 |
| 2020/0232911 | A1* | 7/2020 | Chikugo | G01N 21/27 |
| 2022/0260121 | A1* | 8/2022 | Sato | F16D 27/108 |
| 2023/0061380 | A1* | 3/2023 | Robison | G01D 11/245 |

* cited by examiner

INSTALLATION STRUCTURE FOR GREASE SENSOR

CROSS-REFERENCE TO RELATED APPLICATION

This application claims priority to Chinese Application No. 202211310454.X, filed Oct. 25, 2022, the entirety of which is hereby incorporated by reference.

FIELD

The present disclosure relates to the field of bearing structure and provides an installation structure for grease sensor in bearing structures.

BACKGROUND

Bearings are widely used industrial components to support the rotation of rotating shafts. Bearings may be lubricated by grease. The performance of grease may be gradually reduced due to temperature, load, debris and other factors, resulting in deterioration of the mechanical properties of the bearings. For this reason, it has been proposed in the prior art the use of a grease sensor to monitor the health condition of grease in real time. Usually, a probe of the grease sensor needs to be installed to reach inside the bearing structure to full contact with the grease. The installation structure for the grease sensor is then very important, and if not designed properly, it is easy to causes problems such as grease leakage, shaking or falling off of the sensor, which affects the signal detection accuracy and even the safety of the whole machine. One known installation structure uses threaded fasters to fasten the grease sensor probe onto the housing of the bearing structure, which could not well solve the problem of grease leakage and might be inconvenient to install.

Accordingly, there is a desire in practice to provide an installation structure for the grease sensor which can achieve no-leakage, high stability and convenient installation.

SUMMARY

To overcome at least the above problems, in the first aspect, the present disclosure provides an installation structure for installing a grease sensor, comprising: a housing having a through-hole; a resilient grommet installed in said through-hole, the resilient grommet having an installation hole; and a probe of the grease sensor extending from a base and being inserted into said installation hole such that the end of the probe extends into the interior of the housing to contact the grease inside, wherein the inner surface of the resilient grommet is resiliently pressed against the outer surface of the probe to form a tightly sealing interface.

In some embodiments, the outer surface of the resilient grommet is provided with an annular recess, and the portion around the through-hole of the housing extends into the annular recess.

In some embodiments, the outer surface of the probe is provided with a plurality of sealing projections, against which the inner surface of the resilient grommet is resiliently pressed to form a winding sealing interface.

In some embodiments, the probe has a first limiting surface pressed against the outer surface of the resilient grommet and a second limiting surface pressed against the inner surface of the resilient grommet.

In some embodiments, a first step surface perpendicular to the axial direction of the probe is formed between the probe and the base of the grease sensor, and the first step surface is pressed against the outer surface of the resilient grommet as said first limiting surface.

In some embodiments, the end of the probe is provided with a limiting projection protruding outward from the outer surface, and a second step surface perpendicular to the axial direction is formed between the side of the limiting projection near the housing and the outer surface of the probe, and the second step surface is pressed against the inner surface of the resilient grommet as the second limiting surface.

In some embodiments, the plurality of sealing projections are triangular, trapezoidal, rectangular or semi-circular in cross-section.

In some embodiments, the plurality of sealing projections are two annular projections having a right-angled triangular cross-section, with one right-angled side of the right-angled triangle facing the housing and the beveled side backing away from the housing.

In some embodiments, the resilient grommet is made of oil-resistant elastomeric material.

In some embodiments, the oil-resistant elastomeric material is silicone rubber, fluoro rubber or thermosetting resin.

In the second aspect, the present disclosure provides a bearing structure having the installation structure for installing an grease sensor as above mentioned, wherein the bearing structure comprises a rotating shaft, an inner ring, a rolling element and an outer ring, the inner ring being fixedly attached to the rotating shaft, the outer ring being fixedly attached to the housing, the rolling element being rotatably disposed between the inner ring and the outer ring to provide a rotational support, a gap between the housing and the rotating shaft being filled with grease, and the probe of the grease sensor contacting the grease to detect its condition.

In the third aspect, the present disclosure provides an installation method for a grease sensor using the installation structure as above mentioned, comprising: forming the through-hole on the housing; mounting the resilient grommet in the through-hole; and pressing the probe of the grease sensor into the installation hole of the resilient grommet until the end of the probe extends into the interior of the housing to contact the grease therein, wherein the inner surface of the resilient grommet is resiliently pressed against the outer surface of the probe to form a tightly sealing interface.

The beneficial effects of the present disclosure are as below.

1) A tightly sealing interface could be formed by resiliently pressing the inner surface of the resilient grommet against the outer surface of the probe, thus effectively preventing grease from leaking out through the interface. Advantageously, when the outer surface of the probe is provided with a plurality of sealing projections, the inner surface of the resilient grommet is resiliently pressed against the plurality of sealing projections to form a winding sealing interface, which can further improve the sealing performance.

2) The grease sensor can be installed by inserting the probe of the grease sensor by pushing and pressing it into the installation hole of the resilient grommet, without installing other parts or other processes, thus the installation operation is very convenient.

3) The outer surface of the resilient grommet is provided with an annular recess, and the portion of the housing around the through-hole is disposed within the annular recess, such that the resilient grommet is firmly installed in the housing. Further, the probe has a first limiting surface pressed against the outer surface of the resilient grommet and a second limiting surface pressed against the inner surface of the resilient grommet, so that the probe is firmly installed in the resilient grommet. This structure can realize a stable installation of the grease sensor, avoid accidental displacement or detachment, ensure the accuracy of the detection signal of the grease sensor and improve safety of the whole device.

REFERENCE NUMBERS

Figure 1:
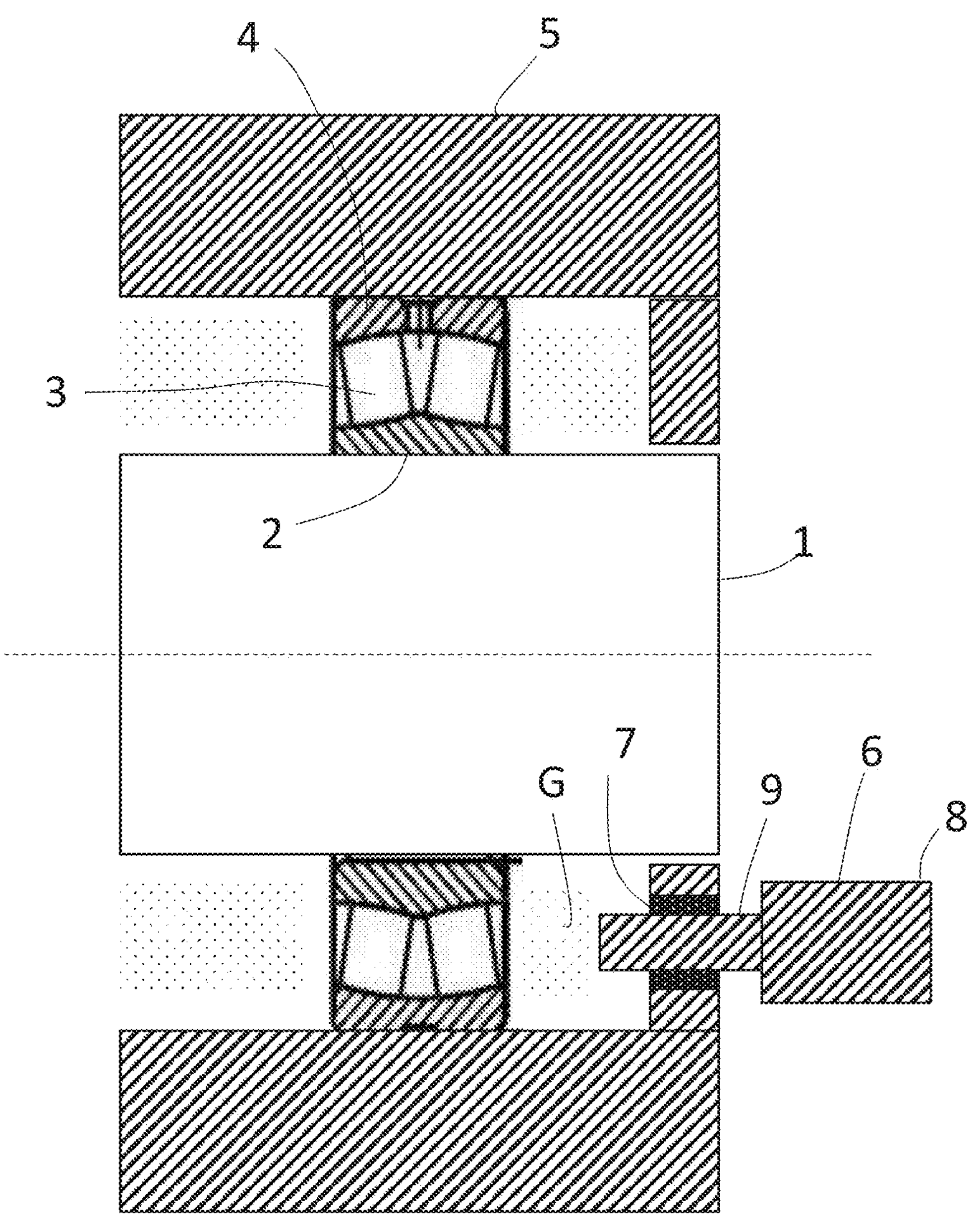
FIG. 1 illustrates a schematic diagram of a bearing structure installed with a grease sensor.

1 rotating shaft;
2 inner ring;
3 rolling element;
4 outer ring;
5 housing;
6 grease sensor;
7 resilient grommet;
8 base;
9 probe;
10 annular recess;
11 annular projection;
12 sealing projection;
13 first step surface;
14 limiting projection;
15 second step surface;
16 guiding bevel;
G grease; and
S sensing element.

DETAILED DESCRIPTION

In order to make the purposes, solutions and advantages of the present disclosure clearer, a detailed description of the technical solutions in the embodiments of the present disclosure will be given below in combination with the drawings thereof. Unless otherwise stated, the terms used herein have the usual meaning in the art. The same or corresponding reference numbers in the drawings refer to the same or corresponding elements.

In order to solve the problems including grease leakage, unstable installation and inconvenient operation caused by the installation of a grease sensor, the present disclosure provides a novel installation structure for grease sensor.

FIG. 1 illustrates a schematic diagram of a bearing structure using the installation structure for grease sensor of the present disclosure. The bearing structure comprises a rotating shaft 1, an inner ring 2, a rolling element 3, an outer ring 4 and a housing 5. The inner ring 3 is fixedly attached to the rotating shaft 1. The outer ring 4 is fixedly attached to the housing 5. The rolling element 3 is rotatably disposed between the inner ring 2 and the outer ring 4 to provide rotational support. It should be noted that the bearing structure as shown is only an example, and other bearing structures as known in the art could be combined with the installation structure of the present disclosure. As shown, the gap between the housing 5 and the rotating shaft 1 may be filled with grease G to provide lubrication to the rotation of the rolling element 3. At a suitable position of the housing 5, such as at the end cap position, a through-hole is disposed for installing the grease sensor 6, and a resilient grommet 7 is fixedly installed in the through-hole. It should be noted that the grease sensor of the present disclosure can be installed in any possible position on the housing, as long as it can contact and detect the grease condition and do not interfere with the bearing structure. Various possible installation positions fall within the scope of protection of the present disclosure. The outer surface of the resilient grommet 7 is in close contact with the inner wall of said through-hole, and the inner wall of the resilient grommet 7 defines an installation hole. The resilient grommet 7 is made of oil-resistant elastomeric material with elastic deformation ability, such as silicone rubber, fluoro rubber, thermosetting resin, etc. In addition, as illustrated in the drawings, the grease sensor 6 has a base 8 and a substantially cylindrical probe 9 extending from the base 8. In the present disclosure, the size of the probe 9 is slightly greater than the size of the installation hole inside the resilient grommet 7.

During installing the grease sensor 6, the probe 9 is inserted into the installation hole of the resilient grommet 7 so that the end of the probe 9 can be in full contact with the grease G inside the housing 5. During this process, the resilient grommet 7 can be elastically deformed outward under pressure to allow the probe 9 to pass smoothly through the installation hole. After the probe 9 is installed in position, due to the resilient recovery force, the inner surface of the resilient grommet 7 may be pressed against the outer surface of the probe 9, forming a tightly sealing interface, which interface can basically eliminate the gap between the probe 9 and the resilient grommet 7, thus effectively preventing the grease G from leaking to the outside.

The above-mentioned resilient grommet 7 and the probe 9 of the grease sensor 6 together constitute the installation structure for grease sensor of the present disclosure, which can be installed by a simple push-in operation and is very convenient to operate. There is no need to mount threaded fasteners at other locations on the housing 5, thereby having little impact on the structure of the housing 5. The resilient deformation capacity of the resilient grommet 7 can allow for convenient insertion reliable suppression of grease leakage.

Figure 2:
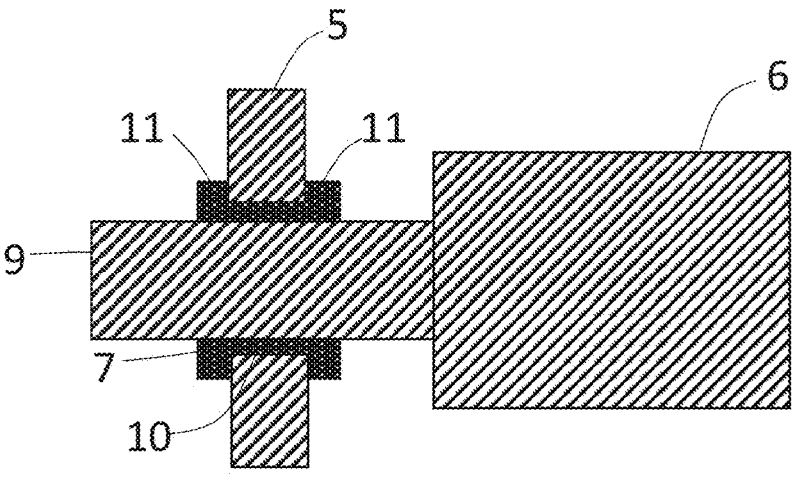
FIG. 2 illustrates a schematic diagram of an installation structure for grease sensor according to the first embodiment of the present disclosure.

FIG. 2 illustrates a schematic diagram of an installation structure for grease sensor according to the first embodiment of the present disclosure. In this embodiment, the resilient grommet 7 is attached to the housing 5 by means of a recess. As illustrated in FIG. 2, the outer surface of the resilient grommet 7 has an annular recess 10 with two annular projections 11 formed on both side along the axial direction. The outer diameter of the annular recess 10 matches the inner diameter of the through-hole in the housing 5, specifically being slightly greater than the inner diameter of the through-hole. The width of the annular recess 10 matches the wall thickness of the housing 5, specifically being slightly smaller than the wall thickness of the housing 4. In this way, when the resilient grommet 7 is installed to the housing 5, the portion of the housing 5 around the through-hole will be positioned into the interior of the annular recess 10, and the two annular projections 11 of the resilient grommet 7 will press against the inner and outer sides of the housing 5, respectively, thereby defining the position of the resilient grommet 7 so that it can be securely installed to the housing 5. Moreover, the interface between the housing 5 and the resilient grommet 7 will be tightly pressed throughout, which effectively prevents the internal grease from escaping along this interface. Since the resilient grommet 7 has sufficient resilient deformation capacity, it can be partially inserted into the through-hole by simple manual operation, and its position can be adjusted around the through-hole of the housing 5, which is a very easy installation operation without additional parts or processes. In addition, as illustrated in FIG. 2, the outer surface of the probe 9 is smooth and cylindrical, and its diameter is slightly greater than the inner diameter of the installation hole inside the resilient grommet 7. In this solution, a flat and straight sealing interface is formed resulting from the resilient compression of the resilient grommet 7 on the outer surface of the probe 9, which can prevent the grease from leaking out.

Figure 3:
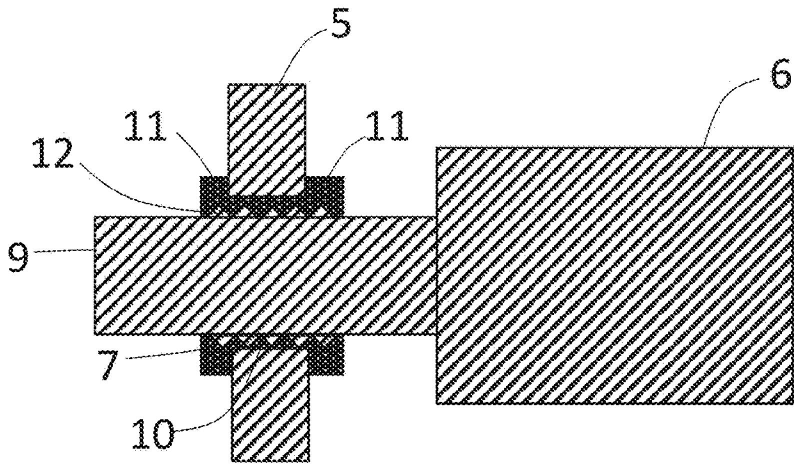
FIG. 3 illustrates a schematic diagram of an installation structure for grease sensor according to the second embodiment of the present disclosure.

FIG. 3 illustrates a schematic diagram of an installation structure for grease sensor according to the second embodiment of the present disclosure, which is essentially the same as the embodiment of FIG. 2, and only the difference between them is described below. Different from the embodiment of FIG. 2, the probe 9 of the grease sensor 6 here does not have a smooth and cylindrical outer surface but has a plurality of sealing projections 12 formed on the outer surface. Therefore, when the resilient grommet 7 is pressed against the outer surface of the probe 9, the interface between the two will be winding rather than flat, and this winding interface will be very beneficial in improving the sealing performance and stopping the grease from leaking out. It should be noted that although FIG. 3 illustrates the cross-section of the plurality of sealing projections 12 here as five connected isosceles triangles, it is only schematic, and the cross-section of other numbers and other shapes, such as trapezoids, rectangles, arcs, semicircles, right triangles, and etc., are feasible and fall within the scope of protection of the present disclosure.

Figure 4:
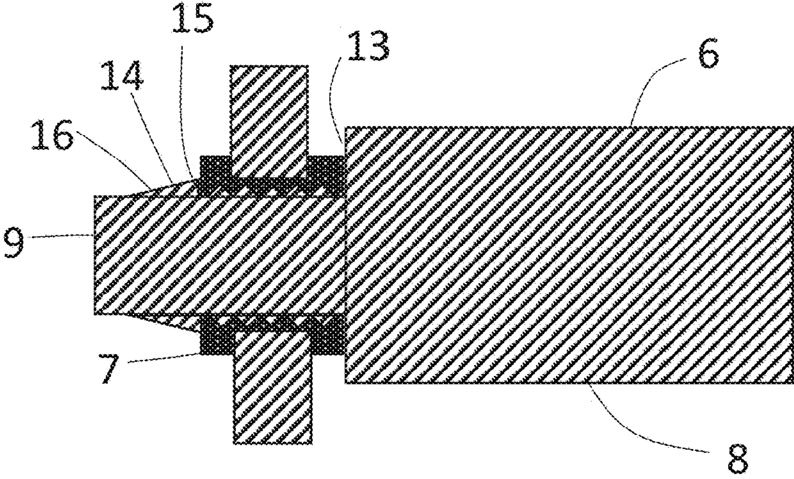
FIG. 4 illustrates a schematic diagram of an installation structure for grease sensor according to the third embodiment of the present disclosure.

FIG. 4 illustrates a schematic diagram of an installation structure for grease sensor according to the third embodiment of the present disclosure, which is essentially the same as the embodiment of FIG. 3, and only the difference between them is described below. Different from the embodiment in FIG. 3, a first step surface 13 perpendicular to the axial direction is formed between the probe 9 and the base 8 of the grease sensor 6, and the first step surface 13 is pressed against the outer surface of the resilient grommet 7 as a first limiting surface to limit the movement of the grease sensor 6 toward the inside of the housing 5. Further, the end of the probe 9 has a limiting projection 14 protruding outward from the outer surface of the probe 9, and a second step surface perpendicular to the axial direction is formed between the side of the limiting projection 14 near the housing 5 and the outer surface of the probe 9, and the second step surface 15 is pressed against the inner surface of the resilient grommet 7 as a second limiting surface to limit the movement of the grease sensor 6 toward the outside of the housing 5. Accordingly, the engagement of the two limiting surfaces of the probe 9 with the resilient grommet 7 make the grease sensor 6 to maintain a stable position in the axial direction, resulting in a reliable installation. Preferably, as illustrated in FIG. 4, on the side of the limiting projection 14 away from the housing 5, a guiding bevel 16 is formed at an acute angle to the axial direction, and the guiding bevel 16 can gradually compress the resilient grommet 7 to deform during the insertion of the probe 9, then guiding the probe 9 to be inserted smoothly into the resilient grommet 7 without significant resistance.

Figure 5:
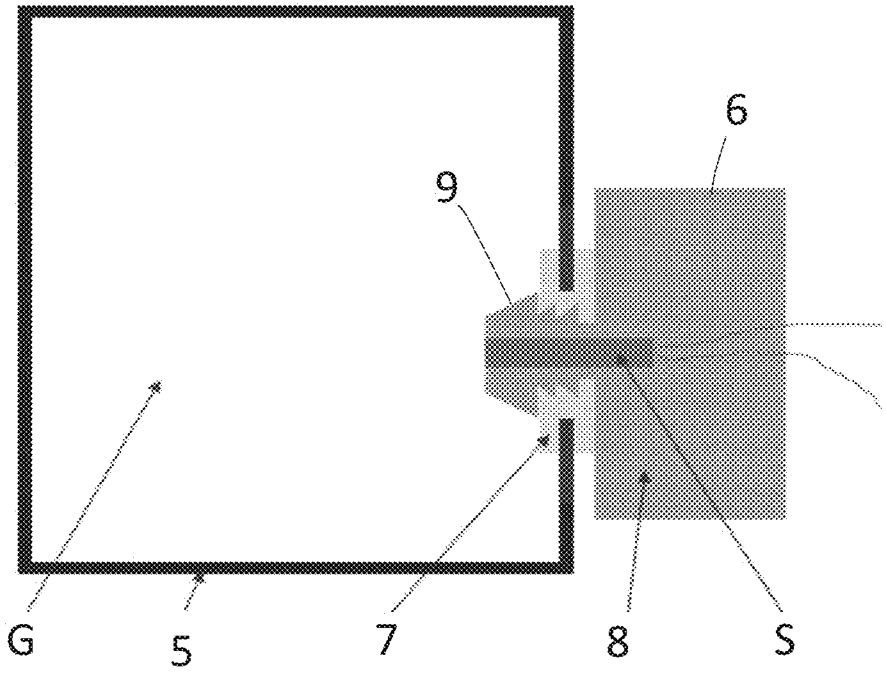
FIG. 5 illustrates a schematic diagram of an installation structure for grease sensor according to the fourth embodiment of the present disclosure.
Figures 6, 7:
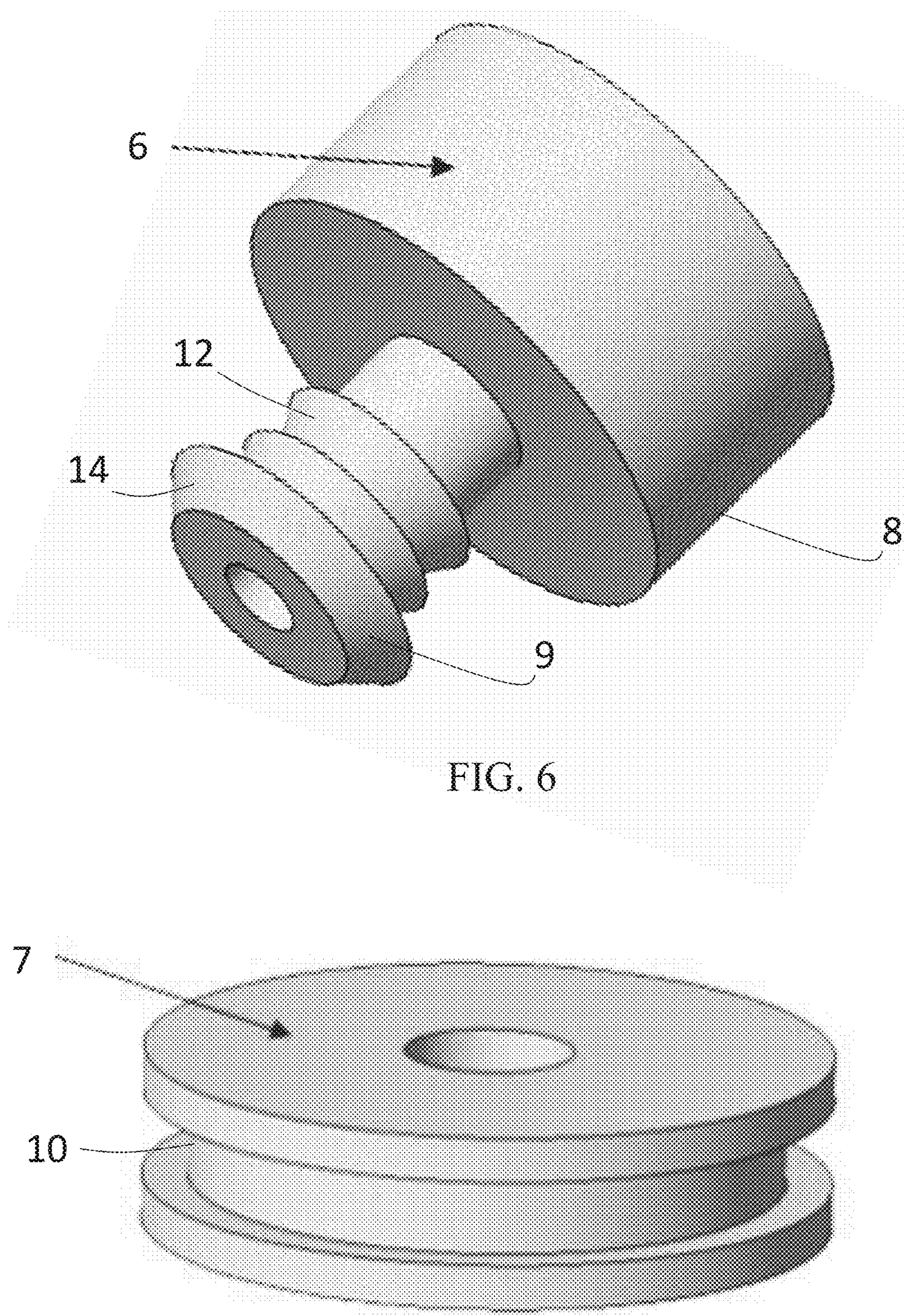
FIG. 6 illustrates a schematic diagram of a probe of the grease sensor.
FIG. 7 illustrates a schematic diagram of a resilient grommet.

FIG. 5 illustrates a schematic view of the installation structure for grease sensor of a specific and preferred embodiment, FIG. 6 illustrates a perspective view of the grease sensor 6 therein alone, and FIG. 7 illustrates a perspective view of the resilient grommet 7 therein alone. This embodiment is essentially the same as the embodiment in FIG. 4, and the difference is mainly in the specific shape of the sealing projection 12 and the limiting projection 14 on the probe 9. As illustrated in FIG. 6, two sealing projections 12 are provided on the outer surface of the probe 9 for engagement with the inner surface of the resilient grommet 7. Each sealing projection 12 has a right-angled triangular cross-section with one right-angled side coinciding with the outer surface of the probe 9 and the other right-angled side perpendicular to the outer surface of the probe 9 and facing the side of the base 8, and the beveled surface forming an acute angle with the outer surface of the probe 9 and facing away from the side of the base 8. The two sealing projections 12 are arranged next to each other, i.e., arranged front to back. Furthermore, as illustrated in FIG. 6, the limiting projection 14 also has a right triangular cross-section and is arranged in the same direction as the arrangement of the sealing projections 12, i.e., its beveled surface forms an acute angle with the outer surface of the probe 9 and faces the side back away from the base 8. Preferably, the height of the limiting projection 14 is greater than the height of the sealing projections 12 so as to form a second limiting surface large enough to provide an effective position limiting force.

FIG. 5 also schematically illustrates a sensing element S located at the center of the probe 9 with the signal and power lines connected thereto. Both the lines are embedded in the material of the base 8. The sensing element S may use various sensors known in the prior art that can measure grease performance parameters, which is not the focus of the present disclosure and therefore will not be described here.

Based on the above installation structure for grease sensor, the present disclosure also provides a novel installation method for grease sensor, which may include the following steps (referring to FIG. 5):

1) forming a through-hole on the housing 5;
2) mounting a resilient grommet 7 in the through-hole; and
3) pressing the probe 9 of the grease sensor 6 into the installation hole of the resilient grommet 7 until the end of the probe 9 extends into the interior of the housing 5 to contact the grease G therein, wherein the resilient grommet 7 is resiliently pressed against the outer surface of the probe 9 to form a tightly sealing interface.

Advantageously, the outer surface of the probe 9 is provided with a plurality of sealing projections 12 and said grease sealing interface is winding in shape.

Advantageously, the above step 2) of the method may comprise: moving a portion of the resilient grommet 7 through the through-hole in the housing 5 and then placing the wall of the housing 5 into the annular recess 10 of the resilient grommet 7 to define the axial position of the resilient grommet 7.

Advantageously, the above step 3) of the method may comprise: pushing the probe 9 of the grease sensor 6 into the installation hole inside the resilient grommet 7 until the first limiting surface of the probe 9 is pressed against the outer side of the resilient grommet 7 and the second limiting surface of the probe 9 is pressed against the inner side of the resilient grommet 7 to define the axial position of the grease sensor 6.

By using the installation structure and installation method of the present disclosure, a convenient installation of the grease sensor 6 can be realized. Only pushing and pressing operation is required during the installation, and no threaded connection or other connection is needed. Moreover, since the sealing interface is formed between the housing 5 and the resilient grommet 7 and between the resilient grommet 7 and the probe 9, the grease leakage can be effectively prevented. Furthermore, since the resilient grommet 7 can mounted on the wall of the housing 5 through the annular recess 10, and the probe 9 can be mounted on the resilient grommet 7 through two limiting surfaces, the installation positions of the resilient grommet 7 and the grease sensor 6 are firm and not easy to be displaced or detached, which improves the reliability of the installation.

The exemplary embodiments of the present disclosure are described in detail here with reference to the preferred embodiments. However, it is understood by those skilled in the art that, without departing from the concept of the present disclosure, multiple variants and modifications can be made to the above specific embodiments, and a variety of combinations of various technical features and structures proposed by the present disclosure can be made without exceeding the scope of protection of the present disclosure, which is determined by the appended claims.

What is claimed is:

1. An installation structure for installing a grease sensor, the installation structure comprising:

a housing having a through-hole;

a resilient grommet installed in said through-hole, the resilient grommet having a first end and an opposite second end, the resilient grommet having an installation hole extending between the first and second ends;

a base; and a probe extending from the base, the probe being inserted into said installation hole such that the end of the probe extends into the interior of the housing to contact grease inside the housing, wherein an inner surface of the resilient grommet is resiliently pressed against an outer surface of the probe to form a tightly sealing interface;

wherein the outer surface of the probe is provided with a plurality of sealing projections, against which the inner surface of the resilient grommet is resiliently pressed to form a winding sealing interface;

wherein the probe has a first limiting surface pressed against the first end of the resilient grommet and a second limiting surface pressed against the second end of the resilient grommet.

2. The installation structure according to claim 1, wherein the outer surface of the resilient grommet is provided with an annular recess, and the portion around the through-hole of the housing extends into the annular recess.

3. The installation structure according to claim 1, wherein a first step surface perpendicular to the axial direction of the probe is formed between the probe and the base of the grease sensor, and the first step surface is pressed against the first end of the resilient grommet as the first limiting surface.

4. The installation structure according to claim 1, wherein the end of the probe is provided with a limiting projection protruding outward from the outer surface, and a second step surface perpendicular to the axial direction is formed between the side of the limiting projection near the housing and the outer surface of the probe, and the second step surface is pressed against the second end of the resilient grommet as the second limiting surface.

5. The installation structure according to claim 1, wherein the plurality of sealing projections are triangular, trapezoidal, rectangular or semi-circular in cross-section.

6. The installation structure according to claim 1, wherein the plurality of sealing projections are two annular projections having a right-angled triangular cross-section, with one right-angled side of the right-angled triangle facing the housing and the beveled side backing away from the housing.

7. The installation structure according to claim 1, wherein the resilient grommet is made of oil-resistant elastomeric material.

8. The installation structure according to claim 7, wherein the oil-resistant elastomeric material is silicone rubber, fluoro rubber or thermosetting resin.

9. The installation structure according to claim 4, wherein the resilient grommet is made of oil-resistant elastomeric material.

10. The installation structure according to claim 9, wherein the oil-resistant elastomeric material is silicone rubber, fluoro rubber or thermosetting resin.

11. A bearing structure having the installation structure for installing a grease sensor according to claim 10, wherein the bearing structure comprises:

a rotating shaft;

an inner ring fixedly attached to the rotating shaft;

an outer ring fixedly attached to the housing;

a rolling element rotatably disposed between the inner ring and the outer ring to provide a rotational support; and a gap between the housing and the rotating shaft being filled with grease, the probe of the grease sensor contacting the grease to detect its condition.

12. A installation method for a grease sensor using the installation structure according to claim 10, the method comprising:

forming the through-hole on the housing;

mounting the resilient grommet in the through-hole; and pressing the probe of the grease sensor into the installation hole of the resilient grommet until the end of the probe extends into the interior of the housing to contact the grease therein, wherein the inner surface of the resilient grommet is resiliently pressed against the outer surface of the probe to form a tightly sealing interface.

13. A bearing structure having the installation structure for installing a grease sensor according to claim 1, wherein the bearing structure comprises:

a rotating shaft;

an inner ring fixedly attached to the rotating shaft;

an outer ring fixedly attached to the housing;

a rolling element rotatably disposed between the inner ring and the outer ring to provide a rotational support; and a gap between the housing and the rotating shaft being filled with grease, the probe of the grease sensor contacting the grease to detect its condition.

14. A installation method for a grease sensor using the installation structure according to claim 1, the method comprising:

forming the through-hole on the housing;

mounting the resilient grommet in the through-hole; and pressing the probe of the grease sensor into the installation hole of the resilient grommet until the end of the probe extends into the interior of the housing to contact the grease therein, wherein the inner surface of the resilient grommet is resiliently pressed against the outer surface of the probe to form a tightly sealing interface.

* * * * *